(12) United States Patent
Zhou et al.

(10) Patent No.: US 8,015,034 B2
(45) Date of Patent: Sep. 6, 2011

(54) CARE PLAN UPDATE MANAGEMENT

(75) Inventors: Bin Zhou, San Jose, CA (US); Yaqiong Fang, Milpitas, CA (US); Daniel Simms, Sunnyvale, CA (US); Imtiyaz Haque, Cupertino, CA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 308 days.

(21) Appl. No.: 12/096,053

(22) PCT Filed: Nov. 15, 2006

(86) PCT No.: PCT/IB2006/054275
§ 371 (c)(1),
(2), (4) Date: Jun. 4, 2008

(87) PCT Pub. No.: WO2007/066248
PCT Pub. Date: Jun. 14, 2007

(65) Prior Publication Data
US 2008/0306771 A1 Dec. 11, 2008

Related U.S. Application Data

(60) Provisional application No. 60/742,292, filed on Dec. 5, 2005.

(51) Int. Cl.
*G06F 19/00* (2006.01)
(52) U.S. Cl. .............................................. 705/3; 705/2
(58) Field of Classification Search .................. 705/1, 2, 705/3; 600/300; 715/763
See application file for complete search history.

(56) References Cited

U.S. PATENT DOCUMENTS

| 6,032,119 | A | 2/2000 | Brown et al. |
| 6,139,494 | A | 10/2000 | Cairnes |
| 6,171,237 | B1 | 1/2001 | Avitall et al. |
| 6,426,759 | B1 * | 7/2002 | Ting et al. ..................... 715/763 |
| 7,034,691 | B1 * | 4/2006 | Rapaport et al. ........... 340/573.1 |
| 2002/0046047 | A1 * | 4/2002 | Budd ................................ 705/1 |
| 2003/0135390 | A1 | 7/2003 | O'Brien et al. |
| 2004/0034288 | A1 * | 2/2004 | Hennessy et al. ............. 600/300 |

(Continued)

FOREIGN PATENT DOCUMENTS

JP 2003-296464 10/2003

(Continued)

OTHER PUBLICATIONS

X.H.Wang, "A Web Based Service for Patients Compliance to Disease Treatment", Proceedings of the 25th Annual International Conference of the IEEE Engineering in Medicine and Biology Society, Concun, Mexico, vol. 4 or 4, Conf. 25, Sep. 17, 2003, pp. 1417-1420.

(Continued)

*Primary Examiner* — Gerald J. O'Connor
*Assistant Examiner* — Natalie A Pass

(57) ABSTRACT

A care plan management system (10) includes a server (12) including a content database (14) containing care management-related content including multiple revisions of at least some said content. Each content revision is tagged with temporal content revision information. A care plans storage (18) stores a plurality of patient care plans (21, 22, 23) associated with corresponding patients. Each patient care plan includes a selection of care management-related content to be presented to the patient, and a revision policy indicating which temporal revision of said content should be presented. User interfaces (31, 32, 33) are operatively connected with a communication interface (28) of the server (12) to receive and present the selected care management-related content.

24 Claims, 6 Drawing Sheets

U.S. PATENT DOCUMENTS

Figure 1:
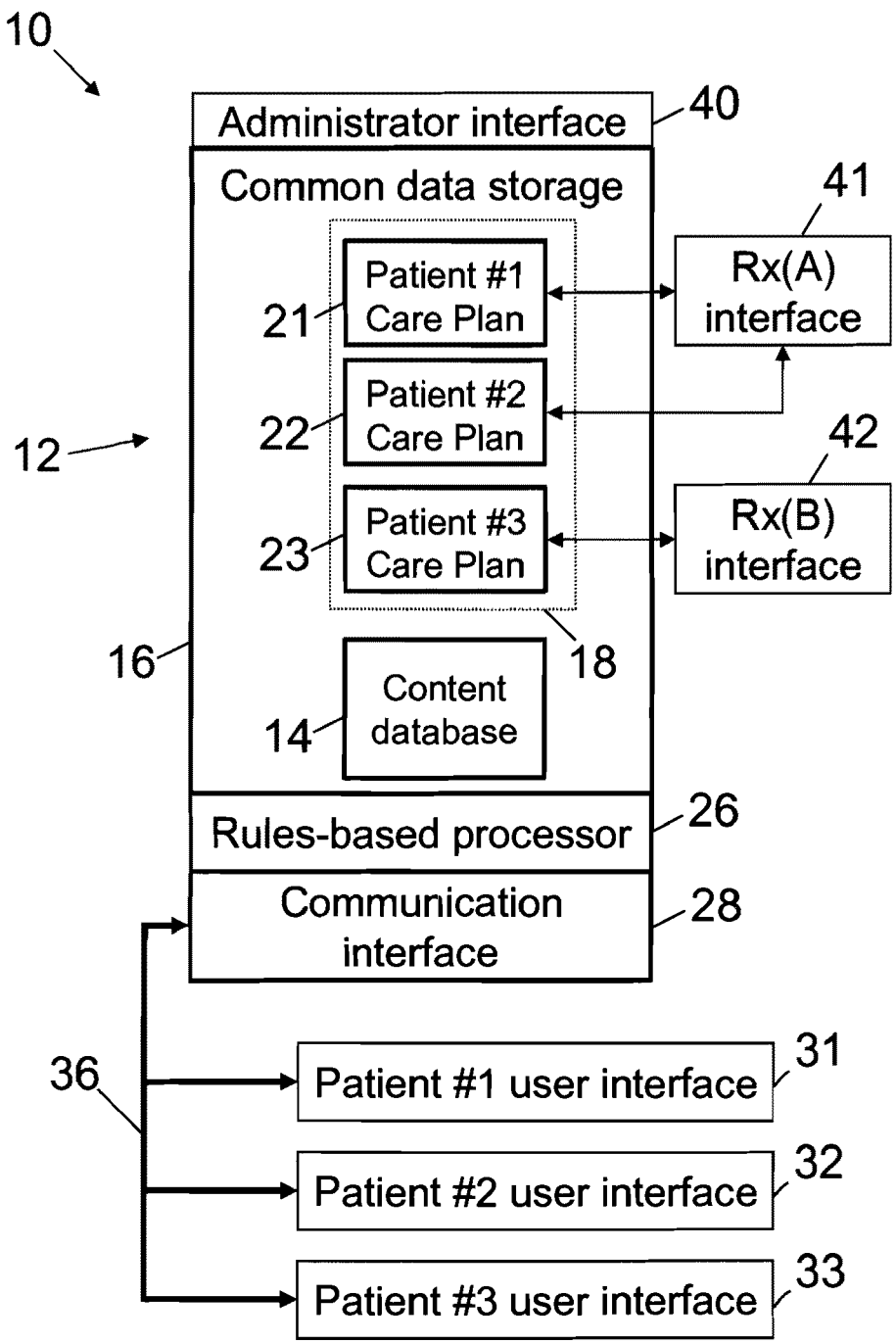

| | | | |
|---|---|---|---|
| 2004/0078231 A1* | 4/2004 | Wilkes et al. | 705/2 |
| 2004/0120557 A1* | 6/2004 | Sabol et al. | 382/128 |
| 2004/0122701 A1* | 6/2004 | Dahlin et al. | 705/2 |
| 2005/0125255 A1 | 6/2005 | Mockett | |
| 2005/0228883 A1 | 10/2005 | Brown | |
| 2006/0047538 A1* | 3/2006 | Condurso et al. | 705/3 |
| 2006/0173985 A1* | 8/2006 | Moore | 709/223 |

FOREIGN PATENT DOCUMENTS

| | | |
|---|---|---|
| WO | WO 0169513 A2 * | 9/2001 |

OTHER PUBLICATIONS

N. Noury, "New Trends in Health Smart Homes", Enterprise Networking and Computing in Healthcare Industry, 5th International Workshop, Jun. 6-7, 2003, pp. 118-127.

D. Johnson, "Converting PC GUIs for NonPC Devices", Circuit Cellur Ink, vol. 91, Vernon, CT, Feb. 1998, pp. 40-42.

N. C. Hulse, "KAT: A Flexible XML-based Knowledge Authoring Environment", Journal of the American Medical Informatics Assoc., vol. 12, No. 4, Philadelphia, PA, Jul. 2005, pp. 418-430.

* cited by examiner

Post-Cardiac Event Care Plan 100

| Content module | Default Revision policy |
|---|---|
| Weight loss module | Latest version |
| Quit Smoking module | Latest version |
| Exercise module | Latest version |
| Fiber module | Latest version |

Intervention rules revision 1.2

Patient data repository template

Fig. 3

Patient #1 Care Plan 21

| Content module | Revision policy |
|---|---|
| Weight loss module | Revision 1.3 |
| Quit Smoking module | Revision 6.2 |
| Exercise module | Latest version |
| Fiber module | Latest version |

Patient #1 data repository

Fig. 4

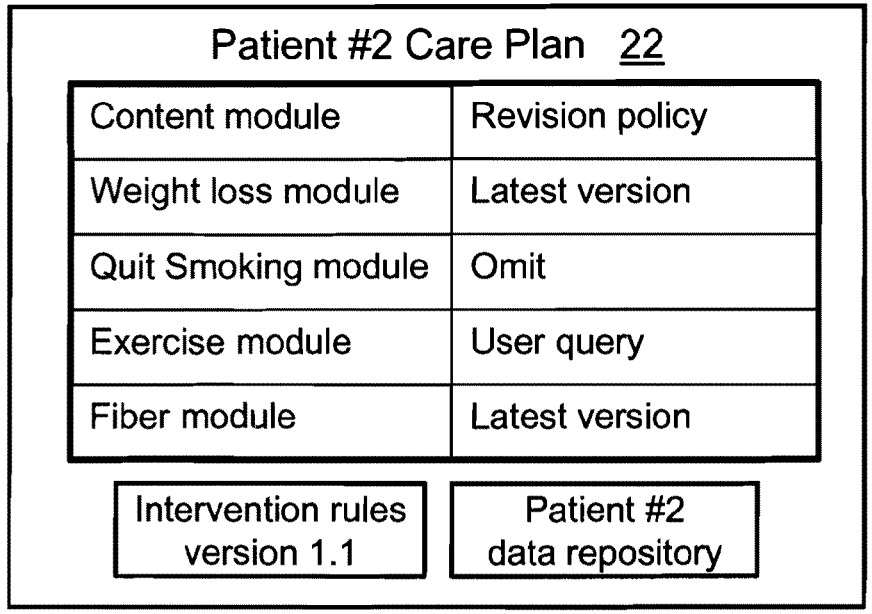

Fig. 5

This module is available in the following versions:

Version 3.7
This version employs the Jazzercise ExerciseBike.
You should select this version <u>only</u> if your ExerciseBike is labeled "<u>Jazzercise</u>."

Version 3.6
This version employs the older version of ExerciseBike.
You should select this version if your ExerciseBike does <u>not</u> include the label "Jazzercise."

Please press "1" to select version 3.7.
Please press "2" to select version 3.6.

Fig. 6

Patient #3 Care Plan

| Content module | Revision policy |
|---|---|
| Weight loss module | Latest version |
| Quit Smoking module | Latest version |
| Exercise module | Latest version |
| Fiber module | Latest version (retro) |

Patient #3 data repository

Fig. 7

Patient #1 Care Plan Activity

| | |
|---|---|
| Monday | Weight loss module  v. 1.3 |
| Tuesday | Exercise  module  v. 3.7 |
| Wednesday | Fiber  module  v. 8.3 |
| Thursday | Quit smoking  module  v. 7.0 |
| Friday | *System Upgrade To:*<br>*Weight loss module v 1.4*<br>*Fiber module v. 8.4*<br><br>Fiber  module  v. 8.4<br>(updated components) |

Fig. 8

CARE PLAN UPDATE MANAGEMENT

The following relates to the health management arts. It finds particular application in conjunction with out-patient management of chronic illnesses such as congestive heart failure, emphysema, chronic obstructive pulmonary disease (COPD), and so forth, and will be described with particular reference thereto. It finds application more generally in conjunction with methods and apparatuses for providing extended-term health management for: chronic diseases; rehabilitation from a catastrophic event such as a stroke or an automobile accident; managing weight; controlling insomnia; redressing health-impacting lifestyle issues such as smoking or poor diet or inadequate physical exercise; avoiding potential medical conditions such as osteoporosis or tooth decay; and so forth.

Medical professionals recognize that providing extended-term health care management assistance to chronically ill patients is an important aspect of treating the chronic illness and assuring the patient a high quality of life. Extended term health management is typically performed on an out-patient basis, and is typically wholly or in large part self-administered, with occasional help from weekly therapy classes or so forth. It is well known, however, that patients often fail to adequately follow the prescribed health care plan outside of a hospital or other medical setting. This failure can result from lack of understanding of how to perform health care activities, apathy or lack of motivation due to depression, fear of failure, or so forth.

Such problems can in principle be overcome by increased one-on-one interaction between the patient and medical personnel. For example, a daily visit to the patient by a traveling nurse could help ensure that the patient is taking medications in a timely fashion and following prescribed dietary and exercise regimens. However, it is often not feasible to provide such intensive one-on-one sessions due to high cost, lack of available medical personnel, or so forth.

In some cases, the patient can choose to access a hospital website or other on-line (e.g., Internet-based) medical database to pull information relevant to the patient's care plan. However, the patient may not have Internet access, or may be unable to navigate a complex on-line medical database. Moreover, providing access to on-line databases does nothing to help patients who are unmotivated. Other approaches that have been used include providing the patient with instructional or motivational videos. However, these approaches do not provide interactive assistance of a type likely to encourage the patient to follow care plan regimens. Moreover, passive videos are difficult to personalize so as to directly address specific issues related to the patient.

Royal Philips Electronics, Cardiovascular Associates of the Delaware Valley, and Comcast Corporation have announced a cooperative effort called Motiva™ to provide a test group of chronic heart failure patients with a remote patient management broadband-enabled platform for connecting the test patients with their healthcare community. The Motiva™ system provides a cable television-based interactive health care management platform, in which content such as educational video, medication scheduling, personalized encouragement and reinforcement, and so forth, is pushed to the patient based on a personalized health care plan. Feedback from the patient, for example through the use of interactive surveys, enables the Motiva™ system to adjust or personalize content to the needs of each patient. The Motiva™ system can deliver personalized health care management assistance to patients on a daily or more frequent basis.

One problem that arises in maintaining such a personalized interactive care management system is timely updating of content while continuously providing personalized care management assistance to large numbers of patients. As medical knowledge and state-of-the-art progresses, the content deliverable by such a system can become outdated. Accordingly, it is useful to update content, or portions of content, to reflect new knowledge, new medical technology, new information, or so forth. However, medical professionals often have differing opinions as to the advisability of following new (and possibly unproven) medical procedures or recommendations, and some doctors may not want certain updated content to be delivered to their patients. Also, on an individual patient basis certain updated content may be inappropriate.

The following contemplates improvements that overcome the aforementioned limitations and others.

According to one aspect, a server is disclosed for a care management system. A content database contains care management-related content including multiple revisions of at least some said content. Each content revision is tagged with temporal content revision information. A care plans storage stores a plurality of patient care plans associated with corresponding patients. Each patient care plan includes: (i) a selection of care management-related content to be presented to the corresponding patient and (ii) a revision policy indicating which temporal revision of said content should be presented to the corresponding patient. At least one communication interface is included for communicating selected care management-related content to patients. The communicated content for each patient is selected based on the corresponding patient care plan, tagged temporal content revision information, and the revision policy of the corresponding patient care plan.

According to another aspect, a care plan management system is disclosed, including a server as set forth in the preceding paragraph, and a user interface operatively connected with the at least one communication interface of the server to receive and present the selected care management-related content.

According to another aspect, a method is disclosed for managing care. Care management-related content is stored, including multiple revisions of at least some said content. Each content revision is tagged with temporal content revision information. A plurality of patient care plans associated with corresponding patients are stored. Each patient care plan includes: (i) a selection of care management-related content to be presented to the corresponding patient and (ii) a revision policy indicating which temporal revision of said content should be presented to the corresponding patient. Selected care management-related content are communicated to patients. The communicated content for each patient is selected based on the corresponding patient care plan, tagged temporal content revision information, and the revision policy of the corresponding patient care plan.

According to another aspect, a computer readable medium or media such as an optical disk, magnetic disk, magnetic tape, random access memory (RAM), read-only memory (ROM), FLASH memory, or so forth, stores a program for managing care. The program when executed by a computer, digital processor, network server, or so forth, or by a combination thereof, performs process operations comprising communicating selected care management related content to a patient. The communicated content for each patient is selected based on a patient care plan, temporal content revision information tagged to the selected care management related content, and a revision policy of the patient care plan.

One advantage resides in balancing currency of a personalized interactive care management assistance system with the flexibility to continue delivering older content to certain patients as appropriate.

Another advantage resides in enabling updating of a personalized interactive care management assistance system substantially simultaneously with continuing delivery of personalized content to patients.

Another advantage resides in providing medical personnel the option to provide, or not provide, revised medical content to their patients.

Numerous additional advantages and benefits will become apparent to those of ordinary skill in the art upon reading the following detailed description of the preferred embodiments.

The invention may take form in various components and arrangements of components, and in various process operations and arrangements of process operations. The drawings are only for the purpose of illustrating preferred embodiments and are not to be construed as limiting the invention.

FIG. 1 diagrammatically shows principal components of a personalized interactive care management assistance system.

Figure 2:
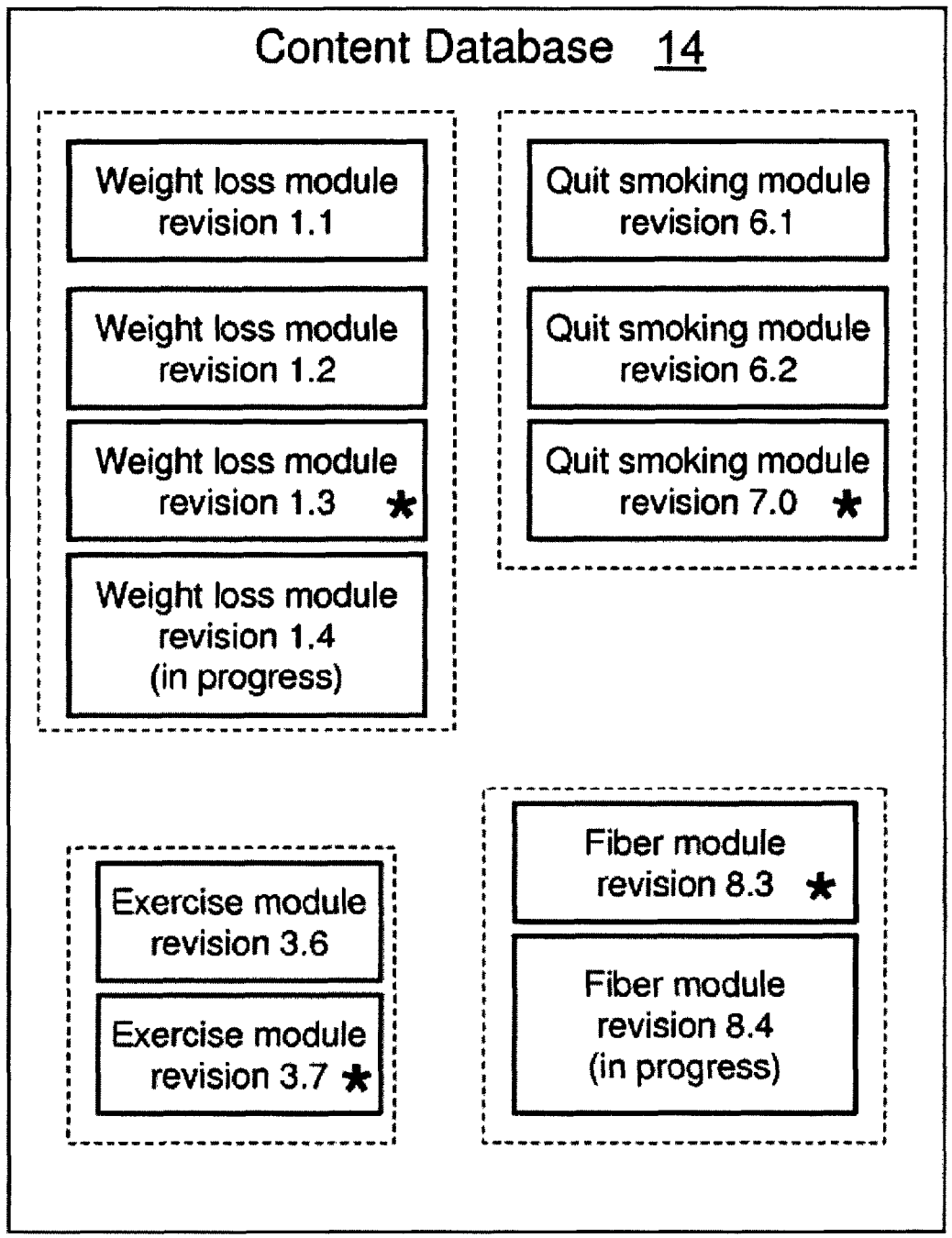

FIG. 2 diagrammatically shows the content modules database of the personalized interactive care management assistance system of FIG. 1.

FIG. 3 diagrammatically shows an example post-cardiac event care plan suitable for assignment to overweight patients who are smokers and who have suffered a traumatic cardiac event such as a heart attack.

FIG. 4 diagrammatically shows the post-cardiac event care plan assigned to Patient #1.

FIG. 5 diagrammatically shows the post-cardiac event care plan assigned to Patient #2.

FIG. 6 diagrammatically shows a user interface display querying Patient #2 to select a content revision based on displayed semantic information contained in the tagged temporal content revision information.

FIG. 7 diagrammatically shows the post-cardiac event care plan assigned to Patient #3.

FIG. 8 diagrammatically shows a five-day period of care plan activity undertaken by Patient #3 in accordance with the post-cardiac event care plan assigned to Patient #3 shown in FIG. 7.

With reference to FIG. 1, a personalized interactive care management system 10 includes a server 12 for distributing care management-related content. In the example system 10, the content is arranged in a content database 14 stored on a common data storage 16. The server 12 can be embodied in various ways, such as by a centralized computer or computer server, a desktop computer, a distributed array of computers, or so forth. The care management-related content typically includes videos, text, surveys, questionnaires, or so forth directed toward assisting in achieving various health management tasks. For example, care management-related content may be provided that are directed toward: reducing weight; stopping smoking; learning to self-administer a medical intervention such as a medication, a biometric monitor, or so forth; learning to follow a dietary restriction such as a low-salt diet; learning to follow a dietary requirement such as a high-fiber diet; performing a physical exercise; or so forth.

To enable personalized distributing of content, each patient in the system 10 has an associated care plan that in the illustrated embodiment is stored in a care plans partition 18 that is also stored on the common system storage 16. The example common data storage 16 is logically partitioned to define the content database 14 and the care plan storage. In the illustrated embodiment, the common data storage 16 stores a care plan 21 for Patient #1, a care plan 22 for Patient #2, and a care plan 23 for Patient #3. While only three care plans 21, 22, 23 associated with a corresponding three Patients #1, #2, #3 are illustrated, it is contemplated that the server 12 may store care plans for a thousand or more different patients. As used herein, the term "patient" encompasses patients recovering from surgery, stroke, heart failure, or another condition, patients suffering a chronic illness that is being treated on an out-patient basis, or so forth. As used herein, the term "patient" also encompasses other users of the health management system 10 who may be generally healthy but who are following a health management program assisted by the system 10 to maintain fitness, control weight, avoid osteoporosis, or otherwise maintain a healthy condition or make health-related lifestyle modifications. Moreover, the use of the partitioned common data storage is one example of many suitable storage arrangements. As another example, in other contemplated embodiments separate storage media may be provided for the content database and the patient care plans.

A rules-based processor 26 determines content to be distributed to each patient based on suitable rules contained in or identified by the patient care plan of that patient. Rules suitably determine which content is presented to which patient or patients, the ordering of such content presentation, and so forth. A communication interface 28 of the server 12 communicates selected care management-related content to selected patients at respective user interfaces. For example: the communication interface 28 communicates content intended for Patient #1 to a user interface 31 that is accessible by Patient #1; the communication interface 28 communicates content intended for Patient #2 to a user interface 32 that is accessible by Patient #2; the communication interface 28 communicates content intended for Patient #3 to a user interface 33 that is accessible by Patient #3; and so forth. The user interfaces 31, 32, 33 can employ substantially any hardware capable of providing content presentation and capable of providing feedback to the server 12 via the communication interface 28. For example, the user interfaces 31, 32, 33 can be embodied by hardware such as: a desktop computer; a laptop computer; a personal data assistant (PDA); a cellular telephone (i.e., cellphone); a television set having Internet connectivity integrally included and operated by a television remote control or other input device; a digital or analog television set having Internet connectivity provided by an add-on set-top unit and operated by a television remote control, set-top unit remote control, or other input device; or so forth. The communication interface 28 is operatively connected with each of the user interfaces 31, 32, 33 by a pathway or pathways 36 such as the Internet, a cable television network, a satellite television network, a cellular telephone network, or so forth. Moreover, the communication interface 28 optionally includes more than one communication interface. For example, it is contemplated for different user interfaces to connect with the communication interface 28 by different pathways each employing different interface hardware and software. For example, the user interface 31 might be a computer operatively connected with the communication interface 28 by the Internet, while the user interface 32 might be a cellphone connected with the communication interface 28 by a cellular telephone network. To construct such an embodiment, the communication interface 28 suitably includes an Internet port component, and a cellular telephone network port. The pathway or pathways 36 are advantageously secure links because private medical information may be conveyed across the pathway or pathways 36. However, unsecured pathways can also be used.

To provide an interactive system, the user interfaces 31, 32, 33 are optionally interactive user interfaces whereby the respective Patients #1, #2, #3 can provide input that is communicated to the server 12 via the communication interface 28. For example, the user interface can be an interactive television set, such as a digital television set or a television set including a set-top box configured to provide interactivity. In other cases, the user interfaces 31, 32, 33 may be a computer, a laptop computer, a personal data assistant (PDA), and a cellular telephone (cellphone), each of which devices provides interactive capability. Feedback provided by the user interfaces 31, 32, 33 may include for example answers to questions posed by the content, or answers to surveys, quizzes, tests, questionnaires, or the like that assess how well the patient or user understood previously presented content. Optionally, the user interface may include one or more biometric feedback monitors each of which measures at least one biometric parameter of an patient that is communicated to the server via the communication interface 28. Suitable biometric monitors may include, for example: a saturated blood oxygen level ($SpO_2$) monitor; a heart rate monitor; a blood pressure monitor; a weight scale; an electrocardiograph (ECG); or so forth.

Maintenance of the server 12 is suitably performed by an administrator via an administrator interface 40. In some embodiments, the administrator interface 40 is suitably a network administrator account having a high level of access to the server 12. The administrator may, for example, add new care management-related content, delete obsolete or outdated care management-related content, organize content, modify or update content flow rules, or so forth. In some embodiments, medical personnel such as doctors or nurses can directly generate and/or update the patient care plans 21, 22, 23 by directly accessing the server 12 via medical personnel interfaces 41, 42. Medical personnel are optionally assigned a lower level of access through a regular user account or other network account providing lower level access limited, for example, to patients of a doctor who is accessing the system 10. For example, the first medical personnel interface 41 accesses the patient care plans 21, 22 of Patients #1 and #2 who are patients of the doctor employing the first medical personnel interface 41, while the second medical personnel interface 42 accesses the patient care plan 23 of Patient #3 who is a patient of the doctor employing the second medical personnel interface 42. In some embodiments, medical personnel interfaces 41, 42 are omitted, and one or more system administrators perform all creation and updating of the patient care plans 21, 22, 23 via the administrator interface 40, and in accordance with instructions from the patient's physician or other medical personnel.

With reference to FIG. 2, the care management-related content stored in the content database 14 is in some embodiments organized into self-contained content modules. FIG. 2 diagrammatically depicts the following example content modules: weight loss module; quit smoking module; exercise module; and high fiber diet module. Each module may be occasionally updated. To enable suitable selection of whether or not to present each user with the updated content, a new module revision is created for each update. Changes in module content justifying creation of a new revision may include, for example, adding new material, adding new components, revising existing material or components to reflect current medical knowledge or updated equipment, or so forth. To enable suitable selection of which content revision to present to each user, each such content revision is tagged with temporal content revision information. For example, the weight loss module has an earliest revision tagged as revision 1.1, a later revision tagged as revision 1.2, and a latest revision tagged as revision 1.3. Additionally, a revision-in-progress is tagged as revision 1.4, and is not yet ready for use. The revision 1.3 is optionally marked as the latest revision (the latest revision of each content module is diagrammatically indicated in FIG. 2 by a large boldfaced asterisk). Alternatively, where the tagged temporal content revision information includes ordering information such as the illustrated revision number tags 1.1, 1.2, 1.3, or as another example an alphabetical revision indicator tagging, the latest content revision can be identified as that content revision whose tagged temporal content revision ordering information indicates the content revision is the latest revision. However, if this latter approach is used, then the revision-in-progress should be numbered "0.0" or otherwise tagged to ensure that it is not inadvertently identified as the latest revision.

The other content modules illustrated as examples in FIG. 2 also have multiple content revisions. The quit smoking module includes three content revisions tagged as revisions 6.1, 6.2, and 6.3, with revision 6.3 marked as the latest revision. The exercise module includes two content revisions tagged as revisions 3.6 and 3.7, with revision 3.7 marked as the latest revision. The high fiber diet module includes one content revision tagged as revision 8.3 and marked as the latest revision, and also includes a revision-in-progress tagged as revision 8.4 which is not yet ready for use.

With reference to FIG. 3, each patient care plan is suitably constructed from a care plan template that is configured for a certain class of patients. FIG. 3 illustrates an example "Post-Cardiac Event Care Plan" 100 that is suitable for assignment to patients within a class of patients who are overweight smokers and who have suffered a traumatic cardiac event such as a heart attack. The "Post-Cardiac Event Care Plan" 100 includes a list of pointers or identifiers of content modules that such a patient should access. These modules include the example weight loss, quit smoking, exercise, high fiber diet modules or others which are appropriate to overweight smokers who have suffered a traumatic cardiac event. For each listed content module, the "Post-Cardiac Event Care Plan" 100 also includes a default revision policy indicating which content revision should be presented. As illustrated, the default revision policy is to show the latest revision of each content module.

The "Post-Cardiac Event Care Plan" 100 further includes a set of intervention rules, optionally also tagged with revision information, such as the illustrated example revision 1.2 tag for the intervention rules of the "Post-Cardiac Event Care Plan" 100. The intervention rules suitably are performed by the rules-based processor 26 of the server 12 shown in FIG. 1 to order the presentation of the listed content modules, to automate actions on behalf of human care team members based on certain patient activities or supplied information, or so forth. For example, if the user interface includes a scale or other way to convey the patient's weight to the server 12, then based on this weight the intervention rules may decide whether or not the patient needs to be presented with the weight loss module. Still further, the "Post-Cardiac Event Care Plan" 100 optionally includes a patient data repository template. This template may define, for example, data partitions in the patient record for storing quiz results, biometric data supplied from the user interface, or so forth.

With continuing reference to FIG. 3 and with further reference to FIG. 4, when the "Post-Cardiac Event Care Plan" 100 is assigned to a specific patient, such as Patient #1, various parameters of the "Post-Cardiac Event Care Plan" 100 are optionally modified. For example, in the patient care plan 21 for Patient #1, the revision policy for the weight loss and quit smoking content modules has been modified to specify a specific content revision of those content modules. Thus, when following the patient care plan 21, Patient #1 will be presented with weight loss module revision 1.3, which also happens to be the latest weight loss module.

However, Patient #1 will be presented with quit smoking module revision 6.2 even though revision 6.3 is the latest revision, because the patient care plan 21 for Patient #1 has modified the revision policy for the quit smoking module to call for the specific quit smoking module revision 6.2. For example, the latest quit smoking module revision 6.3 may instruct the patient to use a nicotine patch if the latest medical recommendations call for using such a nicotine patch. If this is now the most popular method for quitting smoking, then it can be expected that any future revisions of the quit smoking module will also probably call for using a nicotine patch. If, however, Patient #1's doctor does not believe that nicotine patches are a good method for quitting smoking, then Patient #1's doctor can modify the revision policy of the patient care plan 21 as shown in FIG. 3 to call for Patient #1 to see the older quit smoking module revision 6.2 which does not instruct the patient to use a nicotine patch.

There are many other possible reasons why a particular doctor, or a particular patient, may want to specify a particular content revision. For example, Patient #1's doctor may have specified the specific weight loss control module revision 1.3, rather than keeping the default revision policy of using the latest version, because this doctor is concerned that future revisions may instruct patients in some sort of "fad" diet. By specifying the particular revision 1.3, Patient #1's doctor is assured that Patient #1 will receive the weight loss module revision 1.3 which is a known program.

Other doctors, or other patients, may have different revision policies for different content modules.

With reference to FIG. 5, for example, the patient care plan 22 for Patient #2 employs the default latest version revision policy for the weight loss and high fiber diet modules. The patient care plan 22 for Patient #2 employs an "omit" revision policy for the quit smoking module. This optional revision policy omits the content module entirely. This may be appropriate if, for example, Patient #2 does not intend to quit smoking regardless of the medical consequences of this decision.

The patient care plan 22 for Patient #2 also employs a "user query" revision policy for the exercise module. This optional revision policy asks the patient, at the time of presentation of the content module, which revision should be presented. To enable the patient to make an informed choice, the tagged temporal content revision information includes semantic about the revision that is presented to the user as part of the query. For the example exercise module version 3.7, the tagged temporal content revision information includes the following semantic information: "This version employs the Jazzercise ExerciseBike. You should select this version only if your ExerciseBike is labeled 'Jazzercise.'" For the example exercise module version 3.6, the tagged temporal content revision information includes the following semantic information: "This version employs the older version of ExerciseBike. You should select this version if your ExerciseBike does not include the label 'Jazzercise.'"

With continuing reference to FIG. 5 and with further reference to FIG. 6, in accordance with the "user query" revision policy, Patient #2 is presented with a query constructed from the tagged semantic temporal content revision information, and Patient #2 is asked to select between revision 3.6 and revision 3.7. By giving Patient #2 the semantic information contained in the tagged temporal content revision information, Patient #2 can make an informed choice between revision 3.6 and revision 3.7 based on which type of ExerciseBike Patient #2 has. The selected exercise module version is then presented to Patient #2. This "query user" revision policy can be useful in various situations in which the revised content reflects a change in medications, medical equipment, or so forth supplied to the patient. In some embodiments, the patient's doctor or other medical person may have the option of limiting the choices given to the patient in the "user query" revision policy.

With continuing reference to FIG. 5, the patient care plan 22 further includes an intervention rules version number 1.1, which it will be noted is an earlier rules revision than the version number 1.2 included in the baseline "Post-Cardiac Event Care Plan" 100 shown in FIG. 3. As the patient care plan itself, such as the intervention rules, may be revised occasionally, the care plan or components thereof such as the intervention rules include selectable revisions. In the illustrated embodiment, the care plan defaults to using the latest revision policy in which the latest revision of the intervention rules is used; accordingly, a rules revision policy is suitably only included in a specific patient care plan if, as in the example patient care plan 22, an earlier revision is to be used.

With reference to FIG. 7, the example patient care plan 23 for Patient #3 uses all of the default revision policies of the baseline "Post-Cardiac Event Care Plan" 100 shown in FIG. 3, except that the revision policy for the high fiber diet module is modified to "latest version (retro)." This optional revision policy ensures that the patient receives the latest content revision by re-presenting the content module, or at least re-presenting those portions of the content module that are revised, if the content is revised after the patient has been presented with that content module.

With continuing reference to FIG. 7 and with further reference to FIG. 8, operation of the "latest version (retro)" revision policy is described in the context of patient care plan 23 followed by Patient #3. FIG. 8 diagrammatically shows which content module is accessed by Patient #3 on each day of a particular five-day period running from Monday through Friday. On Monday, the weight loss module is accessed. Since the latest revision policy is in effect for this module, the latest weight loss module revision 1.3 is presented. On Tuesday, the exercise module is accessed. Again, the latest revision policy is in effect for this module, and so the latest exercise module revision 3.7 is presented. On Wednesday, the high fiber diet module is accessed. Here, the "latest version (retro)" policy is in effect. The latest revision as of Wednesday is version 8.3, since version 8.4 is still in-progress and is not yet ready for viewing. Accordingly, Patient #3 is presented with the current latest version high fiber diet module revision 8.3 on Wednesday. On Thursday, the quit smoking module is accessed. Since the latest revision policy is in effect for this module, the latest quit smoking module revision 7.0 is presented.

On Thursday night, the server 12 is updated as part of routine maintenance and updating of the server 12. In this updating, the weight loss module is revised to version 1.4, which was previously in-progress. Accordingly, starting on Friday morning, the latest version is weight loss module revision 1.4, rather than the revision 1.3 that Patient #3 accessed on Monday. However, the latest revision policy is not retroactive. Accordingly, Patient #3 is never presented with the updated material of the weight loss module revision 1.4. In some embodiments, the in-progress modules can be designated to permit automatically changing to the updated version. This option may be appropriate where only not yet viewed sessions are updated, where additional sessions are added, and the like.

Additionally, however, the Thursday night updating includes revising the high fiber diet module from version 8.3 to version 8.4, which was previously in-progress. Accordingly, starting on Friday morning, the latest version is high fiber diet module revision 8.4, rather than the revision 8.3 that Patient #3 accessed on Wednesday. Unlike the situation for the weight loss module, the "latest version (retro)" revision policy is in effect for the high fiber diet module in the case of Patient #3. Accordingly, on Friday (or some other time subsequent to the Thursday updating) Patient #3 is presented with at least the updated components of the high fiber diet module revision 8.4. In this instant example, Patient #3's doctor may have selected the "latest version (retro)" revision policy for the high fiber diet module because that doctor is of the opinion that recent developments in medical knowledge of high fiber diets are significant advances, and so Patient #3's doctor wants to ensure that Patient #3 is presented with the latest high fiber diet information.

In the illustrated embodiment, the default revision policy is to use the latest revision. However, other default revision policies can be used. For example, other revision policies can be made default by modifying the defaults specified in the baseline "Post-Cardiac Event Care Plan" 100 shown in FIG. 3. In some embodiments, the patient's doctor may select the default revision policy. For example, a more conservative doctor may select to use an older revision until he or she has seen and approved each new revision. In such embodiments, the doctor may receive notification by email or another automated messaging pathway each time a module assigned to one of his or her patients is revised. The doctor may also choose different revision policies for different patients, taking into account the type of patient, types of modules assigned to the patient, and other relevant information. Still further, other persons besides the doctor optionally may have the ability to set the revision policy for a given patient. For example, the patient, members of the patient's family, other doctors besides the primary doctor, or other interested parties may be given authorization to set or adjust the patient's revision policy.

Moreover, the example revision policies such as specific revision, latest revision, "user query", and "latest revision (retro)" are illustrative examples—the skilled artisan can readily construct other revision policies that are suited for specific situations. For example, another contemplated revision policy is to use information about the patient to define which revision should be presented—for example, a new revision containing subject matter related to women's health may be presented only to female patients. Another contemplated revision policy is to use the latest revision policy unless a retro-condition is met. For example, the patient may be presented with the latest revision unless the patient is an older piece of medical equipment, in which case an earlier revision that is appropriate for the older equipment is used.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

Having described the preferred embodiments, the invention is now claimed to be:

1. A server for a patient care management system, the server comprising:
    a content database containing care management-related content including multiple revisions of at least some said content, each content revision being tagged with temporal content revision information;
    a care plans storage storing a plurality of patient care plans associated with corresponding patients, each patient care plan including: (i) a selection of care management-related content to be presented to the corresponding patient and (ii) a revision policy indicating which temporal revision of said content should be presented to the corresponding patient; and
    at least one communication interface comprising a computer or digital processor configured to communicate selected care management-related content to patients, the communicated content for each patient being selected based on the corresponding patient care plan, tagged temporal content revision information, and the revision policy of the corresponding patient care plan.

2. The server as set forth in claim 1, wherein the revision policy is selected from a group of revision policy options including at least: (i) a specific revision, and (ii) the latest revision.

3. The server as set forth in claim 2, wherein the tagged temporal content revision information includes an indication of which revision is the latest revision, the latest revision policy selecting that content revision indicated as the latest revision.

4. The server as set forth in claim 2, wherein the tagged temporal content revision information includes ordering information, the latest revision policy selecting that content revision whose tagged temporal content revision ordering information indicates the content revision is the latest revision.

5. The server as set forth in claim 2, wherein the group of revision policy options further includes: (iii) omission of the content.

6. The server as set forth in claim 2, wherein the group of revision policy options further includes: (iii) latest revision retroactive, the at least one communication interface re-presenting at least an updated portion of the latest revision under the latest revision retroactive revision policy responsive to an updated latest content revision.

7. The server as set forth in claim 2, wherein the group of revision policy options further includes: (iii) a user-selection policy, the at least one communication interface querying the patient via the communication interface as to which content revision to present and then presenting the user-selected content revision.

8. The server as set forth in claim 7, wherein the tagged temporal content revision information includes semantic information about the revision that is presented to the user as part of the query.

9. The server as set forth in claim 1, wherein the care management-related content of the content database is organized into self-contained content modules, and the revision policy of each patient care plan includes an independent revision policy for each selected content module that indicates which temporal revision of that content module should be presented to the corresponding patient.

10. The server as set forth in claim 1, wherein each patient care plan further includes:
    (iii) intervention rules providing at least a temporal ordering for presentation of the care management-related content to the corresponding patient.

11. The server as set forth in claim 10, wherein the intervention rules are also tagged with temporal content revision information, and each patient care plan further includes (iii) a rules revision policy indicating which revision of intervention rules should be applied for the corresponding patient.

12. A care plan management system comprising:
    a server as set forth in claim 1; and a user interface operatively connected with the at least one communication interface of the server to receive and present the selected care management-related content.

13. The care plan management system as set forth in claim 12, wherein the user interface is an interactive user interface whereby an associated patient can provide input that is communicated to the server via the at least one communication interface.

14. The care plan management system as set forth in claim 12, wherein the user interface is operatively connected with the at least one communication interface of the server via at least one of the Internet, a cable television network, a satellite television network, and a cellular telephone network.

15. The care plan management system as set forth in claim 12, wherein the user interface includes at least one of: a television set, a television set including a set-top box, a computer, a laptop computer, a personal data assistant (PDA), and a cellular telephone (cellphone).

16. The care plan management system as set forth in claim 12, wherein the user interface includes at least one biometric feedback monitor that measures at least one biometric parameter of an associated patient that is communicated to the server via the at least one communication interface.

17. A method for managing care, the method comprising:
(I) storing care management-related content including multiple revisions of at least some said content, each content revision being tagged with temporal content revision information;
(II) storing a plurality of patient care plans associated with corresponding patients, each patient care plan including: (i) a selection of care management-related content to be presented to the corresponding patient and (ii) a revision policy indicating which temporal revision of said content should be presented to the corresponding patient; and
(III) communicating selected care management-related content to patients, the communicated content for each patient being selected based on the corresponding patient care plan, tagged temporal content revision information, and the revision policy of the corresponding patient care plan;
wherein the operations (I), (II), and (III) are performed by a computer or digital processor.

18. The method as set forth in claim 17, wherein the revision policy of each patient care plan is selected from a group of revision policy options including at least: (i) a specific revision policy, (ii) a latest revision policy, (iii) a latest revision retroactive policy, (iv) a user-query revision policy, and (v) a condition-based revision policy.

19. The method as set forth in claim 17, wherein the revision policy of each patient care plan includes a plurality of generally different revision policies each applicable to a different portion of the care management-related content.

20. The method as set forth in claim 19, wherein the different portions of the care management-related content are arranged as self-contained content modules.

21. A computer readable medium or media storing a program for managing care, the program when executed performing process operations comprising:
communicating selected care management-related content to a patient, the communicated content for each patient being selected based on a patient care plan, temporal content revision information tagged to the selected care management-related content, and a revision policy of the patient care plan.

22. The computer readable medium or media as set forth in claim 21, wherein the program when executed further performs process operations comprising:
tagging an updated portion of the selected care management-related content with updated temporal content revision information, the communicating presenting one of the portion or the updated portion of the selected care management-related content to the patient based on the temporal content revision information and the updated temporal content revision information.

23. The computer readable medium or media as set forth in claim 21, wherein the selected care management-related content is arranged as a plurality of self-contained content modules each tagged with temporal content revision information, and the communicating further comprises:
communicating content modules to a patient, the communicated content for each content module being selected based on temporal content revision information tagged to the content module and the revision policy of the patient care plan.

24. The computer readable medium or media as set forth in claim 23, wherein the revision policy of the patient care plan is configured to apply a generally different revision policy for each communicated content module.

* * * * *